United States Patent
Overmyer et al.

(12)

(10) Patent No.: US 10,785,998 B2
(45) Date of Patent: Sep. 29, 2020

(54) METHOD OF USING A CLEANING, DISINFECTING AND LUBRICATING COMPOSITION FOR A DENTAL UNIT OR BEER FLUID ENCOMPASSING SYSTEM

(71) Applicants: Thad J. Overmyer, Danville, KY (US); Michael Overmyer, Danville, KY (US)

(72) Inventors: Thad J. Overmyer, Danville, KY (US); Michael Overmyer, Danville, KY (US)

(73) Assignees: Michael Overmyer, Danville, KY (US); Thad J. Overmyer, Danville, KY (US)

( * ) Notice: Subject to any disclaimer, the term of this patent is extended or adjusted under 35 U.S.C. 154(b) by 136 days.

(21) Appl. No.: 15/793,618

(22) Filed: Oct. 25, 2017

(65) Prior Publication Data

US 2019/0116846 A1 Apr. 25, 2019

(51) Int. Cl.
| | |
|---|---|
| *C07C 31/22* | (2006.01) |
| *A61L 2/18* | (2006.01) |
| *A23L 3/3526* | (2006.01) |
| *A23L 3/3517* | (2006.01) |
| *B67D 1/07* | (2006.01) |
| *C07C 279/26* | (2006.01) |
| *A23L 3/3508* | (2006.01) |

(52) U.S. Cl.
CPC ............ *A23L 3/3526* (2013.01); *A23L 3/3508* (2013.01); *A23L 3/3517* (2013.01); *A61L 2/18* (2013.01); *B67D 1/07* (2013.01); *C07C 31/225* (2013.01); *C07C 279/265* (2013.01)

(58) Field of Classification Search
CPC .... A61L 2/18; A61L 2/24; B67D 1/07; A61C 19/002; C07C 31/225
USPC .................. 433/82, 88; 134/22.19, 36, 102.1
See application file for complete search history.

(56) References Cited

U.S. PATENT DOCUMENTS

| | | | |
|---|---|---|---|
| 4,668,190 A | 5/1987 | Overmyer | |
| 4,695,255 A | 9/1987 | Overmyer | |
| 5,318,443 A | 6/1994 | Overmyer | |
| 5,443,385 A | 8/1995 | Overmyer | |
| 5,785,523 A | 7/1998 | Overmyer | |
| 6,250,920 B1 | 6/2001 | Overmyer | |
| 2003/0186843 A1* | 10/2003 | Staniforth | A61K 9/0075 424/45 |
| 2014/0158641 A1* | 6/2014 | Mukherjee | C02F 1/32 210/764 |
| 2017/0137304 A1* | 5/2017 | Adams | B01D 61/025 |

* cited by examiner

*Primary Examiner* — Nina Bhat
(74) *Attorney, Agent, or Firm* — Michael Overmyer; Thad J. Overmyer

(57) ABSTRACT

A combination of a method using a composition utilized together to disinfect and/or lubricate a fluid encompassing system. A single composition comprising a disinfectant and a lubricant comprises water-alcohol-glycerin-chlorhexidine gluconate.

This composition is used together with a method of purging this fluid encompassing system, adding said composition into said system, and flushing/rinsing said system. This method ensures that this composition is not diluted and that this composition directly contacts the microbial contamination and biofilm in this system.

This method using this composition maintains and controls this system's encompassing fluid chemical and physical properties by disinfecting and/or lubricating said fluid encompassing system and said system's fluid system components comprising of fluid conduit(s), and/or fluid reservoir(s), and/or valve(s), and/or device(s) that connect to this system's fluid system.

11 Claims, No Drawings

METHOD OF USING A CLEANING, DISINFECTING AND LUBRICATING COMPOSITION FOR A DENTAL UNIT OR BEER FLUID ENCOMPASSING SYSTEM

BACKGROUND OF THE INVENTION

A fluid encompassing system that dispenses a fluid or fluids for in vitro and/or in vivo procedures and/or for consumption must be disinfected. Disinfecting this system routinely will help maintain and control the fluid quality of this system's dispensing fluid. When this fluid encompassing system is not disinfected properly, bacterial contaminates remaining in this system will create biofilm, which contaminates this system's encompassing fluid and said system.

Biofilm is a build up of a slimy layer of bacteria that adheres to the surfaces of said system that encompass a fluid. Although many bacteria can grow in a free-living, planktonic state, it is quite common for them to adhere to surfaces by producing extra-cellular polysaccharide or in some cases by means of specialized structures termed holdfasts. The adherent bacteria produce micro-colonies, leading to the development of biofilm, which initially may be composed of only one bacterial type, but frequently develop to contain several bacteria living in a complex community. In fact, every surface exposed to fluids and/or nutrients will become colonized by microorganisms. This formation of bacteria may be harmful and can result to fatality.

A fluid encompassing system's components comprises of fluid conduit(s), and/or fluid reservoir(s), and/or valve(s), and/or device(s) that connect to this system's fluid system. This fluid conduit(s) transports said system's encompassing fluid, the dispensing end product, through said system.

A fluid encompassing system and this system's fluid are both susceptible to biofilm. During the use of this system, a buildup of contaminates, including bacteria, forms within said system's components. These contaminated components bacterially penetrate this system's encompassing fluid. Biofilm affects the fluid quality of said system's end product, the dispensing fluid. When said dispensing fluid becomes bacterial compromised, the properties of said fluid are altered.

The inner walls of these system's components: fluid conduit(s), fluid reservoir(s), and valve(s) are the location of the biofilm and microbial contamination. Free-floating microbes initially adhere to the inner walls of said components and forms a bacterial layer. This microbial layer becomes a growing mass of bacteria. Some bacteria become planktonic and migrate elsewhere in these fluid encompassing components.

Planktonic bacteria forms on rubber, polyurethane, various types of metal, glass, plastic and silicone surfaces which are materials often used for said system's components: fluid conduit(s) and fluid reservoir(s).

Biofilm growth in a fluid encompassing system effects many industries including healthcare, food, hospitality, and water treatment. The build-up of microbial contamination and biofilm in a fluid encompassing system can effect immunosuppressed people, system functions, aerosolization from said system's devices, dispensing's fluid flow, and tastes and odors in dispensing fluid.

Various types of disinfectants are recommended to disinfect said fluid encompassing systems. When a disinfectant is not completely removed from this system, this system's end product, the dispensing fluid's taste, chemical and physical properties are affected from the remnants of the disinfectant and/or contamination from said system.

Bleach based disinfectants are often used to disinfect a fluid encompassing system. If the bleach remnants from the bleach-based disinfectant remain in said system, these bleach remnants will alter the taste of this system's dispensing end product. For example, if this system's dispensing end product was beer, then the beer's taste will be altered from the remnants of the disinfectant in said system.

A method used by only flushing the contaminated fluid conduits with water, does not remove contaminants of the inner walls of this conduit due to laminar flow.

Common methods used to disinfect a fluid encompassing system are to flush a high-temperature-short-time treatment such as pasteurization through this system or flush a pressurized disinfectant through said system. The length of time the disinfectant remains in this system depends on the manufacturer of this disinfectant's recommendation. After a designated period of time, the disinfectant is flushed with pressurized water or this system's end product. The system is now considered disinfected.

Common examples of fluids that encompass a fluid encompassing system: water, milk, medical solutions, liquid admixtures, cold beverages, hot beverages, frozen beverages, sodas, ice cream, yogurt, tea, fruit juice, beer, wine, coffee, consumables, alcohol spirits, liquor, liqueur and other fluids encompass a fluid encompassing system.

Some examples of a fluid encompassing systems are a soda fountain machine, draft beer keg dispensing system, surgical laser system, beverage brewing system, and a dental unit water system.

A dental unit water system will be used as a specific example to explain the importance in disinfecting a fluid encompassing system and how the contributing factors for microbial contamination and biofilm grows in a fluid encompassing system. This system's contaminates effects said system's fluid quality, regardless if the fluid was treated when supplied to said system.

In healthcare, water is a common fluid used with a fluid encompassing system when performing medical/dental procedures upon patients. Water quality is important, especially when water is the dispensing fluid. Water quality is measured in CFU, colony-forming units/mL. This unit of measure is for the number of bacteria colonies found in one milliliter. Heterotrophic bacteria plate count is a procedure for estimating the number of live heterotopic bacteria in the water. Colonies may form in pairs, clusters or single cells, which can be termed as "colony-forming units".

Dental unit water is the dental unit water system's encompassing fluid that is used for dental operative procedures. All dental unit water including treated dental unit water are susceptible to biofilm. The CDC (Centers for Disease Control), recommends that dental unit water used in non-surgical procedures measures less than or equal to 500 colony forming units of heterotrophic bacteria per milliliter (≤500 CFU/mL) of water, which is also the standard set for drinking water by the EPA (Environmental Protection Agency), APHA (American Public Health Association), and the AWWA (American Water Works Association).

A dental unit water system's components comprises of fluid conduit(s) are dental unit waterlines; fluid reservoir(s) are dental water bottle(s) and/or dental water heater(s); valves; and the device(s) are dental handpieces and three-way syringe(s).

The dental water bottle is a reservoir for the dental unit water. The dental water bottle is attached to the dental unit manifold. This manifold has a dental unit waterline called a dental water bottle pick-up tube that transports the dental unit water from the dental water bottle to the handpieces and three-way syringes.

Dental unit waterlines (DUWLs) are narrow-bore tubing used to deliver dental unit water for high-speed dental handpieces, air-water syringes, and dental unit water quick disconnects.

Biofilms are found in dental unit waterlines as a result of microbial contamination. Microorganisms adhere to the inner tubal walls of these waterlines. The ADA (American Dental Association) confirms research showing that a dental unit had high microbial counts as high as 200,000 CFU/mL within 5 days of installing new dental unit waterlines.

Microbial contamination and biofilm inside the dental unit water system affects the dental unit water quality. When the dental unit water becomes bacterial penetrated by the contaminated dental unit water system, this dental unit water's taste, composition and water quality are altered.

A combination of any of the following encourages rapid growth of microorganisms in the dental unit water system: stagnant dental unit water, warm dental unit water temperatures, dental water heaters, small dental unit waterlines tubing diameter, dead ends on dental unit, backflow of oral fluids from patient, handpiece connectors disconnected, poor hygienic ethics by dental office staff, contaminated dental water bottle pick-tube, contaminated dental water bottles, and dental unit water source.

Stagnant dental unit water remaining in this dental unit water system's components creates biofilm. The small lumen of the dental unit's waterlines and the small amount of dental unit water used for dental procedures creates stagnant water, which increases the contamination of the dental unit water. This contamination forms on the inner walls of the dental unit waterlines, passages of valves and other said components with dental unit water flow.

A dead end is a blocked waterline within the dental unit. A dead end on a dental unit is a point at which the dental unit water does not continuously flow and is stopped by a valve. A dead end is a reservoir for bacteria if not properly disinfected.

Dead end examples are the water quick disconnect, slow speed handpiece waterline and/or a water pressure gauge connected to a waterline.

Backflow of oral fluids from a patient is caused when a dental high-speed handpiece's turbine creates a vacuum that sucks the patient's oral fluids back into this handpiece, which leads to contaminating the dental unit waterlines.

Contamination in the dental unit water system can occur when a dental office has poor hygienic ethics by not following protocols, not disinfecting dental unit water system, not washing hands properly, and not wearing gloves. Even if a staff member is wearing gloves, the gloves are not sterile. A staff member can cause contamination within the dental unit water system when touching dental system's components.

When handpiece connectors are disconnected, these connectors are exposed and susceptible to contamination from aerosolization of bacteria contaminates in dental operatory and being touched by staff members.

There are many examples how the dental water bottle pick-up tube becomes contaminated. When re-attaching the dental water bottle to the dental unit, the pick-up tube's external surfaces are contaminated when a staff member touches this pick-up tube when inserting said tube inside the dental water bottle. The staff members' gloves are not sterile. This pick-up tube's contaminated external surface leads to further contamination in the dental unit water of the dental water bottle. Furthermore, this contaminated dental unit water contained by a dental water bottle will then contaminate this bottle.

When the dental water bottle is not attached to the dental unit, the pick-up tube becomes exposed to aerosols and atmospheric contaminants. This is an example of pick-up tube contamination.

The high-density polyethylene (HDPE) plastic dental water bottles are susceptible to bacteria. Dental unit water remaining in a dental water bottle becomes stagnant, a contributing factor to biofilm growth. Microorganisms adhere to the inner walls of the dental water bottle. Another example of a contaminated dental water bottle is when the inside of the dental water bottle are not being disinfected on a routine basis before filling it with dental unit water source.

All dental unit water sources are susceptible to biofilm. Dental unit water without an antimicrobial agent will become more contaminated than water treated with an antimicrobial agent. The common dental unit water sources are municipal water, distilled water, spring bottled water, and well water.

The municipal drinking water source is treated with chlorine, an antimicrobial agent, to ensure this water is a safe drinking water for the community. However, not all cities have quality drinking water. Depending on the geographic area, some cities may have hard municipal water.

When dental offices have hard municipal water for their dental unit water, the hard water mineral deposits: calcium, magnesium, and iron contribute to biofilm growth in the dental unit, clog dental unit waterlines, and cause a low water flow from the high-speed handpieces and air-water syringes. These mineral deposits from the hard municipal water can also impact the life span of some dental cleaning products; however, the present invention's method and composition are not affected by a dental office's water source.

Distilled water source and spring bottled water source have a 24-hour shelf life once opened, since they do not contain an antimicrobial agent.

Dental offices in the rural areas that use well water as their dental unit water source do not contain any antimicrobial agents.

All dental unit water sources including treated dental unit water are susceptible to biofilm. Examples of treated dental unit water: municipal water, filtered water, UV treated water, purified water, spring bottled water, and distilled water.

The dental water treatment products do not disinfect dental unit waterlines. Presently, a common misconception in dentistry is the difference between water treatment products and dental waterline disinfectants.

Dental water treatment products only treat dental unit water. Water treatment products and treated dental unit water do not remove biofilm from the dental unit waterlines.

For example, treated dental unit water is supplied to contaminated dental unit waterlines. This treated dental unit water becomes bacterially penetrated and contaminated when contacting the contaminated dental waterlines, which increases the microbial CFU count in this dental unit water. This results with contaminated dental unit water dispensed for dental procedures.

Dental waterline disinfectants maintain and control the dental unit water quality by cleaning the microbial contamination and biofilm from the dental unit water system. Dental waterline disinfecting products do not treat dental unit water.

Biofilm occurs in the dental unit even with treated dental unit water is present. Therefore, water treatment products refer in their product instructions to use a dental waterline disinfectant to 'shock' the dental waterlines. The term, "shocking" is a marketing term created and replaced the word, "disinfect". Shocking means to disinfect the dental unit waterlines.

The water treatment products refer to use a dental waterline disinfectant since water treatment products only treat dental unit water, and do not disinfect the biofilm from the dental unit waterlines, which helps maintain and control the dental unit water quality.

Most common water treatment products exist in the form of tablets, water filters, cartridges, straws, and water purification systems.

Filters have no effect on biofilm in dental unit waterlines. Dental unit water passes through the porous material in order to separate particulates or biological matter. Matter separated depends on the physical characteristic of the filter material. To remove most bacteria, filters must have a pore of 0.2 microns or less. A filter is found in various locations of the dental unit water system depending on the type of filter. Filters collect planktonic bacteria and the filter can become blocked from not being disinfected or replaced with a new filter. The blockage filter is an example of a dead end, which is a blocked water passage within the dental unit water system, which increases the microbial CFU count in the dental unit water. The life span of this filter depends on the quality of dental unit water. The dental unit water system with a filter usually remains connected to municipal water.

Another form of a water treatment product is a resin filled cartridge impregnated with chemicals that function by the dental unit water or air passing through the cartridge on the chemically impregnated resin. The dental unit water and/or air picks up the chemical agent. This cartridge method requires using a dental waterline disinfectant periodically to remove biofilm in the dental unit water system to ensure effectiveness of the cartridge.

Ultra violet lights improves the quality of incoming dental unit water by killing bacteria that pass in front of the UV light in the waterline. The UV light does not have an effect on biofilm in the dental unit water system.

Water distillers may improve dental unit water quality. This water treatment method is used with any dental unit equipped with dental water bottles. If dental unit waterlines and dental water bottles are not properly maintained and the distiller malfunctions, this water treatment method will produce bacterially contaminated water.

Chemicals for continuous water treatment mixed with dental unit water inactivate suspended bacteria. This water treatment method is usually used continuously during patient treatment, but has little to no effect on biofilm in the dental unit water system.

The present invention's method combined with using this invention's chemical composition is used for an intermittent treatment that maintains and controls the dental unit water quality by disinfecting the microbial contamination and biofilm in the dental unit water system. This method using this composition is compatible with all dental units and is performed while patients are not present in the operatory, therefore resulting with a flush/rinse of said system that does not impact dental operative procedures and does not result in patient exposure to said composition, microbial contamination and biofilm when this method is using said composition. In conclusion, dental unit water treatment products have no effect on the biofilm growth in the dental unit water system. All dental unit water including treated dental unit water are susceptible to biofilm growth regardless of the dental unit water source used and if a water treatment product treated the dental unit water.

The dental unit water system must be disinfected routinely with a disinfectant regimen such as this invention's method using this invention's composition in order to help maintain the CDC's recommend dental unit water quality standards.

Earlier in my U.S. Patents:
1. U.S. Pat. No. 4,668,190 I disclosed a liquid admixing apparatus for dental water-injection systems. Liquid admixing means for a dental oral water-injection system are provided for introducing an additive liquid from a reservoir through an additive tube into a water conduit in the water-injection system wherein a valve in the additive tube can be opened and closed remotely by manually operable means.
2. U.S. Pat. No. 4,695,255 I disclosed a method of cutting and lubricating human hard tissue during power tool cutting wherein the tissue subjected to cutting has directed against it a liquid admixture of water as a cooling agent, alcohol as an anti-infection agent and glycerin as a lubricant.
3. U.S. Pat. No. 5,318,443 I disclosed a method of flushing, disinfecting a dental turbine handpiece by forcing a pressurized solution of a disinfectant and lubricant simultaneously through an air drive line to the handpiece when is not in operation to flush dental debris through an exhaust line.
4. U.S. Pat. No. 5,443,385, I disclosed a method of disinfecting and lubricating a discrete dental-medical device which comprises immersing the device in a water-alcohol-glycerin-chlorhexidine solution which includes methylcellulose as a lubrication-enhancing and film-forming agent and polyglycol as an antifoaming agent, followed by autoclaving the device.
5. U.S. Pat. No. 5,785,523 I disclosed a system integral with a dental unit. This improved system flushes and disinfects all waterlines of the dental unit.
6. U.S. Pat. No. 6,250,920 I disclosed a system that is detachable to purge a dental unit. This portable system can be taken from one dental unit to another dental unit to flush and disinfect the primary waterline and devices.

Neither of my prior art references discloses a combination of both a method and a composition used together to disinfect and/or lubricate a fluid encompassing system.

SUMMARY OF THE INVENTION

The present invention provides a combination of both a single composition comprising a disinfectant and a lubricant combined with this invention's method of using said composition for the application in comprising to disinfect and/or lubricate a fluid encompassing system.

This present invention provides a single composition comprising a disinfectant and a lubricant which comprises about 25% to 75% by volume of water, about 5% to 35% by volume of alcohol, about 10% to 50% by volume of glycerin, and about 0.06% to about 2.0% by volume of chlorhexidine gluconate. This composition's ingredients are water-soluble that does not leave residue and does not create corrosion within said system.

The present invention also provides a method using this invention's composition comprising of purging said system, adding said composition into empty said system, and flushing/rinsing said system. This method ensures that this composition is not diluted and that this composition directly contacts the microbial contamination and biofilm in this system. This method using this composition lubricates this fluid encompassing system, which improves this system's operation and efficiency.

A fluid encompassing system, such as a dental unit water system, may have fluid system components comprising of fluid conduit(s), and/or fluid reservoir(s), and/or valve(s), and/or device(s) that connect to this system's fluid system. These components will become contaminated and susceptible to biofilm growth if not disinfected properly.

These components for a fluid encompassing system such as a fluid reservoir(s) such as a dental water bottle and/or thermos bottle can also be discrete fluid reservoirs that encompass a fluid independently with and/or without a fluid encompassing system. The term, "discrete" as used herein means a reservoir being disconnected from other systems and handled as a separate unit and/or a reservoir that does not require a system and independently encompasses a fluid. This invention discloses how to disinfect this discrete reservoir independently encompassing a fluid with and/or without a fluid encompassing system with this invention's method using this composition.

This contaminated fluid encompassing system and system's components will bacterially penetrate and contaminate this system's encompassing fluid. Disinfecting this system and components routinely with this invention's method of using this composition helps maintain and control this system's encompassing fluid physical and chemical properties.

This invention provides a preparatory schedule performing this method using this composition for a fluid encompassing system that have high microbial counts of microbial contamination and biofilm in order to prevent clogging of the system's fluid conduit(s) when removing the high counts of microbial contamination and biofilm from this system.

This method's first step, purging fluid encompassing system, removes said system's encompassing fluid by a gravity-fed system; and/or a pressurized gas; and/or purging with pressurized gas combined with vacuum suction.

This method's second step, adding this invention's composition into this fluid encompassing system's empty components ensures this composition is not diluted and that this composition directly contacts the microbial contamination and biofilm in this system. This composition remains in the system for a period of time to have an effect upon the microbial contamination and biofilm.

Furthermore, this composition will remain in said fluid encompassing system and components when this system is not being utilized comprising of consecutive days until this system is ready to be utilized again.

After this period of time of disinfecting this system and components is complete, this method's final step, flushing/rinsing said system adds a fluid into said system's fluid system components comprising of fluid conduit(s) and/or fluid reservoir(s). Water may be used as a fluid to flush/rinse system; and/or flushing/rinsing said system is achieved by using a pressurized gas; and/or this method of flushing/rinsing said system is achieved by a gravity-fed system.

The importance that this invention's method combined with this invention's composition are utilized together routinely helps disinfect and control the microbial contamination and biofilm within this fluid encompassing system and components.

DESCRIPTION OF THE PREFERRED EMBODIMENT

It is appropriate to define the terms used herein for the ingredients of this invention's composition that is combined with this invention's method of using this composition.

This composition's ingredient, water, is treated by a ultra-violet light, deionization, filtration, reverse osmosis, and a water softening process in order to ensure this treated water is considered pure, which helps maintain the efficacy of the ingredients in this composition. Untreated water used as an ingredient for this composition affects the chemical properties of this composition.

This composition's ingredient, alcohol, is a denatured ethanol, which comprises spearmint or peppermint as denaturants. This composition's denaturants, peppermint and spearmint, are flavoring agents that indicate when this invention's method using said composition is performed incorrectly. If a mint taste from said composition's flavoring agent(s) are present in said system's end dispensing fluid, then this indicates said system was not purged completely before adding said composition.

This composition's ingredient, chlorhexidine gluconate, is a disinfectant and is commercially available in liquid form as chlorhexidine.

This composition's ingredient, glycerin, is a lubricant, other than a petroleum-based product. Glycerin lubricates this fluid encompassing system, which improves this system's operation and efficiency. Glycerin is a very useful plasticizer and helps maintain the flexibility of said fluid conduit(s) that may be comprised of polyurethane, rubber, plastic, and silicone material. Glycerin is a trihydric alcohol and a humectant. This glycerin is a commercial kosher grade suitable for human consumption.

This composition's ingredients glycerin and the alcohol denaturants help masks the foul odors that are caused by this contaminated fluid encompassing system.

This composition's ingredients: chlorhexidine gluconate and alcohol (glycerin, a trihydric alcohol, and the ethanol alcohol) are preservatives for this composition.

This composition's percentage volumes of the glycerin (trihydric alcohol), and chlorhexidine gluconate are this composition's disinfectant ingredients when formulated together. This method using this composition creates both a physical and chemical reaction on the microbial contamination and biofilm in this fluid encompassing system.

A physical reaction occurs when this method using said composition's disinfectant ingredient, glycerin, also a humectant, attracts water from within the biofilm cell structure causing a change in the physical properties.

A chemical reaction occurs when this method using said composition's disinfectant ingredient, chlorhexidine gluconate, alters the biofilm.

This composition may include a cosmetic ingredient, a coloring agent, which comprises about 0.0002% to about 0.0005% by volume of its content in said composition. This composition's coloring agent serves as an indictor to show a different color from said system's encompassing fluid.

This invention's method while using this invention's composition addresses the microbial contamination and biofilm growth in a fluid encompassing system and components: fluid conduit(s), fluid reservoir(s), valve(s) and device(s) that connect to this system's fluid system. This system and components become contaminated regardless if this system's encompassing fluid quality is treated based on the many aforementioned factors that contribute to biofilm growth in this system, such as a slow moving fluid in the system, the system's stagnant fluid and from human contamination.

Purging this system is important to be performed as the first procedure of this invention's method. The purpose of this method's first step, purging fluid encompassing system, removes the encompassing fluid from this system and components. This removal of the system's existing fluid ensures that this composition is not diluted and that this composition directly contacts the microbial contamination and biofilm within said system.

This composition is specially formulated to disinfect the microbial contamination and biofilm in this system when using this invention's method. Diluting this composition will alter this composition's effectiveness and chemical and physical properties. For example, if the encompassing fluid was not removed before adding composition into this system, then the system's encompassing fluid would be an unwanted additional ingredient to this composition. If the system's encompassing fluid is not removed then it weakens this invention's composition.

Furthermore, removing this system's encompassing fluid from this system ensures that this composition directly targets the microbial contamination and biofilm in said system. The biofilm in the system is a build up of microbial contamination on the surfaces of this system's components. The removal of the system's encompassing fluid by this purging method allows this composition to contact the microbial contamination that is attached to the inner walls of the fluid conduits, fluid reservoir(s), and valves.

This method of purging said system removes said system's encompassing fluid by a gravity-fed system; and/or a pressurized gas; and/or purging with pressurized gas combined with vacuum suction. This method's second step using this composition adds this composition into this fluid encompassing system's empty components. For example, this composition is added into empty fluid reservoir(s) and/or fluid conduit(s). This composition is not diluted, since the system's encompassing fluid was removed by purging. This composition contacts the surfaces of the system's components. Microorganisms adhere to these surfaces.

This composition remains in the system for a period of time to have an effect upon the biofilm. Important to note, this composition will remain in said fluid encompassing system and components when this system is not being utilized comprising of consecutive days until this system is ready to be utilized again.

After this period of time of disinfecting this system and components is complete, this method's final step is flushing/rinsing said system. The purpose of this final step is to remove said composition, microbial contamination and biofilm from this system, which prevents exposure to consumers of dispensing fluid and also prevents the broken down biofilm to build up again if it is not removed from system.

This flushing/rinsing method adds a fluid into said system's fluid system components comprising of fluid conduit(s) and/or fluid reservoir(s). Water may be used as a fluid to flush/rinse system; and/or flushing/rinsing said system is achieved by using a pressurized gas; and/or this method of flushing/rinsing said system is achieved by a gravity-fed system.

The combination of this method using said composition improves said system's operation and efficiency by prolonging the life span of this fluid encompassing system and this system's components which comprises by lubricating said valve(s) helps maintain the functioning of said system. This method disinfects said system by directing said composition upon the microbial contamination and biofilm on the surfaces of this system and said system's fluid system components. The method maintains and controls said system's fluid quality by said composition disinfecting said system's fluid component(s) before said fluid flows through said system. The method using this composition eliminates odor and foul tasting bacteria from said system and improves the flow of said system's encompassing fluid.

This method using this composition for said system that has never been disinfected with this method using said composition and/or said system contains high microbial counts of microbial contamination and biofilm comprises a four week preparatory schedule. If a different method using a different schedule comprising one aggressive treatment was used to remove this system's high counts of microbial contamination and biofilm, then this will likely clog this system's fluid conduits.

The purpose of this preparatory schedule avoids this clogging by gradually breaking down the microbial contamination and biofilm in this system over the course of comprising four weeks while using this invention's method using multiple consecutive treatments of this composition each week. The first week, this method using said composition is consecutively performed every day when said system is utilized during said first week. This method using said composition will be performed comprising twice per week comprising weeks from the second week through the fourth week. After the fourth week, this method using said composition will be performed on said system routinely comprising once per week.

This method used to disinfect a pressurized fluid encompassing system connects this system's component(s) to the pressurized gas. A pressurized gas is connected to this composition's reservoir(s). This pressurized reservoir is then connected to the fluid encompassing system's fluid conduit to be disinfected. This system's pressurized reservoir will allow this composition to flow into this system when the end valve is opened. This composition remains in this system for a period of time. After this period of time, this method's final step is flushing/rinsing said system. The purpose of this final step is to remove said composition, microbial contamination and biofilm from this system, which prevents exposure to consumers of dispensing fluid and also prevents the broken down biofilm to build up again if it is not removed from system.

A method using this composition to disinfect and/or lubricate wherein a fluid encompassing system is a dental unit water system; whereas said system's encompassing fluid is dental unit water; the fluid conduit(s) are dental unit waterlines; the fluid reservoir(s) are dental water bottle(s) and/or dental water heater(s); valves; and the device(s) are dental handpieces and three-way syringe(s).

The present invention's method combined with using this invention's chemical composition is used for an intermittent treatment that maintains and controls the dental unit water quality by disinfecting the microbial contamination and biofilm in the dental unit water system. This method using said composition lubricates this system's valves and improves said system's operation and efficiency. This method using this composition is compatible with all dental units and is performed while patients are not present in the operatory, therefore resulting with a flush/rinse of said system that does not impact dental operative procedures and does not result in patient exposure to said composition, microbial contamination and biofilm when this method is using said composition.

Understanding the basic mechanics of this dental unit water system will ensure that all of the dental unit waterlines are disinfected. A major concern of disinfecting the dental unit waterlines is to begin disinfecting from the dental unit water source of the dental unit water system. For example, municipal water should begin at this system's junction box and dental unit water bottle systems should begin with the dental water bottle.

Dental unit water systems containing a bottle system that obtains dental unit water from a municipal or well water source should begin disinfecting the primary waterline located at this system's junction box. Dental unit water systems that do not disinfect this primary waterline from the junction box give the misconception that all the dental unit waterlines will be disinfected. The dental unit waterline from the junction box to the bottle system is not disinfected. Therefore, the dental unit is still contaminated. These dental bottle systems can be modified using a remote activated routing valve to correct the problem. Standard dental water bottle systems that switch between municipal and bottled water are not designed to disinfect the dental unit waterline from the junction box.

Dental unit water systems utilizing dental water bottles that do not have an air purge feature on this system requires an extra step to this invention's method. The dental water bottle must be emptied to perform the air purge portion of this method. It is very important that this dental water bottle be disinfected before adding the dental unit water to this dental water bottle and also this dental water bottle is disinfected before using this method to disinfect this dental unit water system.

Furthermore, this invention's method eliminates any dental unit waterline "dead ends" or features that "by pass" parts that have water flow into them. Also, disinfecting the dental unit waterlines to the quick disconnect outlet for the cavitron or hydrocolloid system.

In dental units there are open outlets, operable closed outlets and dead ends, an end waterline that is normally kept closed and can only be opened by a system. These outlets must be manually opened to allow the air to force the water out. The dead ends within the dental unit must be opened by a system or the dead end must be removed. Not opening up a water line and preventing the disinfecting process increases contamination to the entire dental unit's water and system.

Many dental units are equipped with a water quick disconnect outlet, a dead end. Water quick disconnect, a dental unit waterline, is very often neglected in disinfecting and is addressed in this invention's method. It is important that the dental waterline to the quick disconnect is not overlooked as it becomes a harbor for bacteria and will keep the CFU count elevated in the dental unit water.

When a waterline from the block to the handpiece connector will not be used to supply dental unit water to the handpiece, this waterline should be disconnected and the block plugged. Otherwise, this waterline will hold stagnant dental unit water, a source of bacteria, which will contaminate the dental unit water system.

Also, if a dental unit water system has dental water heater, this dental water heater must be turned off before disinfecting this system. Warm dental unit water temperatures contribute to biofilm growth in this system.

It is important to understand the mechanics of each dental unit water system to ensure this system is fully disinfected before using this invention's method and composition.

This invention's method's first step is to remove all of the dental unit water from the dental unit water system comprising of purging with a pressurized gas; and/or purging with pressurized gas combined with vacuum suction, which purging this system comprises of purging handpiece waterlines; and/or purging dental water heaters; and/or purging the waterline to said dental water system's quick disconnect; and/or purging dental water bottle(s); and/or purging dental unit waterlines.

Compressed air is an example of pressurized gas to purge this dental unit water system. Deliver clean compressed air into the dental unit's initial waterline site. This initial site may be a waterline coming from a municipal source or from a dental water bottle. This compressed air must be distributed from this initial site through the complete dental unit's water system: dental water bottle(s), dental unit waterlines and valves. The dental water bottle is empty and is attached to the dental unit. Purge dental waterlines by activating this system's devices: handpiece hoses and three-way syringes until dental unit water is eliminated.

Purging system is a critical step to this dental unit waterline disinfecting method. Purging system removes the dental unit water from system before adding this invention's composition. Adding this composition into an empty dental unit water system ensures said composition is not diluted and also that this composition comes into direct contact the surfaces of this system's components: dental unit waterlines, dental water bottles and valves. The microbial contamination and biofilm is attached to these walls.

This method's second step using said composition adds this composition into said dental unit water system components comprising of dental unit waterlines; and/or dental water bottle(s); and/or valves. This step allows this composition to directly target the system's surfaces containing the microbial contamination and biofilm. This composition also lubricates this system's valves that are encompassed by said composition.

In the beginning, this second step addresses disinfecting the dental water bottle and this dental water bottle's pick-up tube, which are the beginning sources of bacteria growth in the dental water system.

In order to disinfect a dental water bottle, this composition is added into an empty dental water bottle(s) while placing a bottle closure or using a clean cloth over said dental water bottle's opening. Rotate said dental water bottle(s) upside down to an inverted position comprising one time to coat the internal surfaces of this contaminated dental water bottle with said composition while said cloth and/or bottle closure is covering over said dental water bottle opening. A cloth that is saturated with said composition is used to wipe down the exterior surface of the contaminated dental water bottle's pick-up tube and internal surface of the dental unit's manifold. Coating this dental water bottle and pick-up tube with this composition will breakdown microorganisms that adhere to these surfaces.

Attach this dental water bottle containing said composition to the dental unit manifold. When the dental water bottle with this composition becomes pressurized and the ends of the dental waterline are opened, this composition will be conveyed from this dental water bottle into this system's valves and dental water lines. The handpiece hoses and three-way syringes are activated causing this composition to exit the dental unit's waterlines end, the valves controlling the flow of said composition through the dental unit's water system is stopped and/or the pressure to the dental water bottle is stopped. The staff member will recognize that this composition exiting this system's devices is this composition containing a coloring agent ingredient to differentiate from the dental unit water. This indicator confirms that dental unit waterlines are filled with this composition and that the staff member performed this method's first step correctly by removing the dental unit water by purging this system before adding this composition.

Allow said composition to remain in said dental water bottle while attached to dental unit comprising 8 hours and/or a period of time. If an additional dental unit water bottle is being disinfected simultaneously as the other dental water bottle is being disinfected while attached to the dental unit, then seal this additional dental water bottle with a clean bottle closure.

When this period of time is fulfilled, dispose remaining said composition and rinse dental water bottle with water after said composition has disinfected said system and components comprising of dental water bottle, dental waterlines, and valves.

This invention's method's final step of flushing/rinsing said dental unit water system is necessary to disinfect said system by removing comprising this invention's composition, microbial contamination and biofilm from this dental unit water system. This method's final step adds a fluid into said dental unit water system to flush/rinse components comprising of dental waterlines and/or said empty clean dental water bottle(s) for flushing/rinsing said dental unit water system for a designated period of time.

This method's final step may use water as a fluid for flushing/rinsing said dental unit water system. The dental water bottle is filled with a water source and this dental water bottle is attached to dental unit. Filling the dental water bottle with water and opening the controlling valves of the dental waterlines will cause pressurized dental unit water from this dental water bottle to go through the waterlines expelling said composition, microbial contamination and biofilm.

This method of flushing/rinsing said dental unit water system could be achieved by using a pressurized gas as fluid; and/or a gravity-fed system. The dental water bottle is empty and attached to the dental unit. An example of using compressed air as a pressurized gas, whereas this compressed air pressurizes the empty dental water bottle and opens the controlling valves of the dental waterlines causes the pressurized air to go through the dental waterlines expelling said composition, microbial contamination and biofilm from this system. This dental unit water system is now disinfected. Fill this system with preferred dental unit water and begin dental procedures.

After this invention's method using said composition comprising to disinfect said system is completed, this composition's ingredients, glycerin and the denaturants from the denatured ethanol, help masks the foul odors that are caused by the microbial contamination and biofilm in said contaminated system.

Biofilm will still grow in this dental unit water system regardless of the dental unit water source and water treatment products used in the dental office. Establishing standards for dental unit water quality is part of the equation; however, even if a dental office takes precautions to disinfect their dental unit water source, this step does not address the microorganisms in the dental unit water system and components: dental unit waterlines, valves and dental water bottles. This system and components become contaminated regardless if the dental unit water is treated based on the many aforementioned factors that contribute to biofilm growth in this system, such as a slow moving dental unit water, the system's stagnant dental unit water and from human contamination.

Dental offices should implement this invention's method while using this composition into their infection control protocol routinely in order to disinfect and control the microbial contamination and biofilm in this dental unit water system to ensure quality dental unit water is provided to patients that consistently meets the recommended CDC water standards. This method using this composition lubricates this dental unit water system, which improves this system's operation and efficiency.

Disinfecting and lubricating this system routinely with this invention's method and composition helps maintain and prolong the life span of this system and components. Industries that use a fluid encompassing system must also use a disinfecting regimen such as this invention's method using this invention's composition in order to address the microbial contamination and biofilm in this system and components.

Components for a fluid encompassing system such as a fluid reservoir(s) can also be discrete fluid reservoirs that encompass a fluid independently with and/or without a fluid encompassing system. The term, "discrete" is used herein means a reservoir being disconnected from other systems and handled as a separate unit and/or a reservoir that does not require a system and independently encompasses a fluid. Examples of a discrete fluid reservoir are dental water bottles, thermos, canteens, cask, non-dishwasher safe reservoirs, reservoirs with long reservoir necks, mixing tanks, vats, kettle, teapot, pot still, a distillation apparatus, and other fluid encompassing reservoirs.

This invention's method using this composition wherein a fluid reservoir(s) is a discrete reservoir independently encompassing a fluid with and/or without a fluid encompassing system comprising this method of using said composition to disinfect said discrete reservoir. Add said composition into this empty discrete reservoir while placing said reservoir's closure on said reservoir's opening or place a clean cloth over said reservoir's opening. Rotate said reservoir upside down to an inverted position comprising one time to coat the inner walls of this reservoir with said composition while said cloth or said reservoir's closure is covering said reservoir's opening. Allow said composition to remain in said reservoir while sealed with a clean container closure for a period of time. When this period of time is fulfilled, dispose remaining said composition and rinse said reservoir with water after said composition has disinfected said reservoir.

This invention's method using this composition is also applied to disinfect and/or lubricate a draft beer keg dispensing system, another common example of a fluid encompassing system.

This method using this composition wherein the draft beer keg dispensing system's encompassing fluid is draft beer; wherein said beer system's components comprising the fluid conduit(s) are keg beer line(s) and/or pressurized gas line(s); the fluid reservoir(s) are beer keg(s), and/or pressurized said composition container(s), and/or pressurized gas cylinder(s); the valve(s) are a keg coupler(s) and/or pressure regulator(s); and the device(s) are a dispensing beer faucet(s) and/or dispensing beer faucet handle(s). Draft beer, the encompassing fluid for a draft beer keg dispensing system, flows through a keg line, a fluid conduit, from the keg beer, a fluid reservoir, to the dispensing beer faucet, a device.

The contamination in this beer system is a build up of biofilm on the surfaces of this system's components. If the contamination remains in said beer system, these contaminates will alter the beer's taste, unless this invention's method of using this invention's composition is performed routinely to disinfect this beer keg system, which will provide the consumer a consistent quality of beer that is not bacterially penetrated and contaminated.

This method using said composition comprises to disinfect said beer system and is compatible with all draft beer keg dispensing systems by comprising with said method resulting with a flush/rinse of said system that does not impact the taste, chemical and physical properties of said system's end dispensing fluid, draft beer, and does not result in consumer consumption to said composition and contamination when performing this method using said composition comprises the following steps This method's first step is to purge said beer system by removing all of the existing beer from beer faucet and keg line. This first step comprises of purging said beer faucet(s); and/or purging said keg line(s) that is unattached from beer keg(s) by using a clean coupler(s) that is attached to a pressurized gas cylinder(s).

This method's second step of using said composition adds this composition by using a clean coupler(s) from the said pressurized composition container(s) into empty keg line(s). This second step comprises of filling keg line(s) with said composition; and/or immerses valve(s) comprising contaminated keg beer coupler(s) and/or beer faucet handle ball bearing mechanism(s) with said composition. Saturate clean cloth with said composition and wipe down the external beer faucet(s) opening. After said composition has disinfected said valve(s), dispose remaining said composition and rinse said valve(s) with water.

This method's final step is flushing/rinsing said beer system to remove said composition and contamination from this beer system. This method's final step adds a fluid into said beer system's components comprising of keg line(s) for flushing/rinsing said beer system. This method's final step may use water as a fluid for flushing/rinsing said beer system; and/or a pressurized gas; and/or a gravity-fed system.

Fluid encompassing systems must be disinfected, because they are susceptible to microbial contamination and biofilm growth. This invention's method using this composition performed routinely disinfects and controls the microbial contamination and biofilm in this system, which ensures this system's end product, the dispensing fluid is not contaminated. This method using this composition lubricates this fluid encompassing system, which improves this system's operation and efficiency. Disinfecting and lubricating this system routinely with this invention's method using this composition helps maintain and prolong the life span of this system and components.

We claim:

1. A method of cleaning, disinfecting and lubricating a contaminated pressurized dental unit water system wherein said dental unit system components include dental unit water lines, dental unit water bottle, dental unit water heater, dental unit valves, dental hand piece, three way syringes and water outlets wherein said components of the dental unit is fluidly connected to a water supply system for said dental unit system comprising the steps of:
   a.) preparing an aqueous cleaning, disinfecting, and lubricating solution comprising 5-35% by volume of alcohol, 10-50% by volume of glycerin, 0.06-2% by volume of chlorhexidine gluconate, dye and a flavoring agent;
   b.) purging the dental water system with compressed air to purge and evacuate water from said dental unit system;
   c.) introducing the aqueous cleaning, disinfecting and lubricating solution of step a.) into the dental unit water supply system to clean, sanitize control contamination on the internal surfaces of the dental unit system components;
   d.) purging the dental unit after passing the aqueous cleaning, disinfecting and lubricating solution through the water supply system by introducing compressed air into the system;
   e.) flushing and rinsing the dental unit system with pressurized water to remove any remaining debris in the dental unit system.

2. The method of claim 1, wherein the alcohol is ethanol, and the aqueous solution of step a.) further comprises a humectant.

3. The method of claim 1, wherein the glycerin is a non-petroleum based glycerin.

4. The method of claim 1 wherein the flavorant is denatured alcohol.

5. The method of claim 1 wherein the dye is a food grade dye which changes the color of the aqueous solution indicating passage of said aqueous cleaning, disinfecting and lubricating through the water system of said dental unit system.

6. The method of claim 1, wherein the aqueous cleaning, disinfecting and lubricating solution has a pH between 4.0-6.5.

7. A method for disinfecting and lubricating a pressurized draft beer keg dispensing system, wherein said draft beer keg dispensing system in combination with the beer keg, beer keg delivery lines, couplings and taps in fluid communication comprising the steps of:
   a.) preparing an aqueous cleaning, disinfecting and lubricant solution comprising 5-35% by volume of alcohol, 10-50% by volume trihydric alcohol and humectant, 0.06-2% by volume of chlorhexidine gluconate, dye and flavoring agent;
   b.) purging lines from draft beer keg dispensing system;
   c.) introducing the cleaning, disinfecting and lubricating aqueous solution of step a. into said draft beer keg dispensing system wherein said aqueous solution when contacting the beer keg dispensing fluid system cleans, disinfects and lubricates said fluid components of said beer keg dispensing system.

8. The method of claim 7, wherein the cleaning, disinfecting and lubricating solution trihydric alcohol and humectant is glycerin.

9. The method of claim 7, wherein cleaning, disinfecting and lubricating solution dye is in an amount of 0.0002-0.0005% by volume of the solution.

10. The method of claim 7, wherein the pH of the cleaning, disinfecting and lubricating solution is between 4.0 and 6.5.

11. The method of claim 7, wherein the dye is used as a color indicator for indicating that the cleaning, disinfecting and lubricating solution has passed through the fluidic connections of the beer dispensing system.

* * * * *